(12) United States Patent
Kinouchi et al.

(10) Patent No.: US 7,297,129 B2
(45) Date of Patent: Nov. 20, 2007

(54) BED-SIDE INFORMATION SYSTEM

(75) Inventors: Yohsuke Kinouchi, Tokushima (JP);
Yasuhiro Kuroda, Tokushima (JP);
Masatake Akutagawa, Tokushima (JP);
Toshiya Okahisa, Tokushima (JP);
Yoshiaki Ohnishi, Tokushima (JP)

(73) Assignee: Koninklijke Philips Electronics N.V., Eindhoven (NL)

( * ) Notice: Subject to any disclaimer, the term of this patent is extended or adjusted under 35 U.S.C. 154(b) by 136 days.

(21) Appl. No.: 10/545,999

(22) PCT Filed: Feb. 6, 2004

(86) PCT No.: PCT/IB2004/000406

§ 371 (c)(1),
(2), (4) Date: Aug. 18, 2005

(87) PCT Pub. No.: WO2004/074966

PCT Pub. Date: Sep. 2, 2004

(65) Prior Publication Data

US 2006/0161091 A1    Jul. 20, 2006

(30) Foreign Application Priority Data

Feb. 19, 2003  (JP) .............................. 2003-040931

(51) Int. Cl.
*A61M 37/00* (2006.01)
*A61B 5/02* (2006.01)
(52) U.S. Cl. ..................... 604/4.01; 600/481; 600/485; 128/925
(58) Field of Classification Search ................. 600/573, 600/481, 483, 485, 504; 604/5.01; 128/925
See application file for complete search history.

(56) References Cited

U.S. PATENT DOCUMENTS

| 5,533,511 A | 7/1996 | Kaspari |
| 5,810,759 A | 9/1998 | Merz |

FOREIGN PATENT DOCUMENTS

| EP | 0 997 103 A1 * | 5/2000 |
| EP | 1 364 666 A1 * | 11/2003 |
| WO | WO 02/053209 A1 * | 7/2002 |
| WO | WO 03/000125 A1 | 1/2003 |

* cited by examiner

*Primary Examiner*—Max Hindenburg
*Assistant Examiner*—Jonathan M Foreman

(57) ABSTRACT

An object of invention is to display necessary information on a screen and display predicted information obtained by predicting the progression of the necessary information. In a bed-side information system, a body information monitor 11 measures arterial blood pressures of a patient 14. The body information monitor 11 measures systolic arterial blood pressures and diastolic arterial blood pressures, and calculates average values thereof. A Hematocrit monitor 12 calculates Hematocrit, change blood volume rate, and Venous Blood Oxygen Saturation. The body information monitor 11 transmits arterial blood pressure information to a desktop PC 15 and the Hematocrit monitor 12 transmits Hematocrit, change blood volume rate, and Venous Blood Oxygen Saturation to the desktop PC 15. The desktop PC 15 displays arterial blood pressure, Hematocrit, change blood volume rate, and Plasma Refilling Rate on a screen of a display using these information items.

18 Claims, 10 Drawing Sheets

| | | CURRENT | 10 MIN. LATER | 20 MIN. LATER | 30 MIN. LATER | ... |
|---|---|---|---|---|---|---|
| ABP [mmHg] | SYSTOLIC | 126 | 120 | 124 | 116 | |
| | DIASTOLIC | 64 | 62 | 61 | 58 | |
| Ht[%] | | 32.1 | 32.8 | 33.4 | 33.6 | |
| ΔBV%[%] | | — | -2.1 | -3.9 | -4.5 | |
| PRR[l/hr] | | — | -0.13 | -0.18 | -0.24 | |

BED-SIDE INFORMATION SYSTEM

BACKGROUND OF THE INVENTION

1. Field of the Invention

The present invention relates to a bed-side information system, particularly to a bed-side information system which is able to display necessary information on a screen.

2. Description of the Related Art

It has been conventionally impossible to observe information on the human body such as a patient and information on blood processing in real time and simultaneously. To solve this problem, the present inventors have constructed a system which acquires body information and information on blood processing in real time when blood purification is in progress and controls the information appropriately.

However, when the above-described apparatus is used, for example, to prevent a blood pressure drop due to a drastic variation in water balance when blood purification is in progress, there is a problem that blood pressure information is not displayed on a screen and it is difficult to grasp their correlation.

Furthermore, there is also a growing demand for predicting the progression of necessary information and adopting appropriate measures in response to the predicted value. To meet this demand, a system capable of also displaying predicted information obtained by predicting a state several hours ahead on a screen is required.

The present invention has been implemented taking into account the above described points and it is an object of the present invention to provide a bed-side information system capable of displaying necessary information on a screen and displaying predicted information obtained by predicting the progression of the necessary information on the same screen.

SUMMARY OF THE INVENTION

To achieve this object, a bed-side information system according to the present invention comprises body information acquiring means for acquiring body information of a patient, blood purifying means for purifying blood of the patient, the blood purifying means having a blood circuit for circulating the blood, blood information acquiring means for acquiring blood information obtained from the blood, the blood information acquiring means connecting to the blood circuit and display means for displaying the body information and the blood information, the display means connecting to the body information acquiring means and the blood information acquiring means, and is characterized in that the display means has a managing table for managing the body information and the blood information, and displays the body information and the blood information on a screen according to the managing table.

This configuration allows all information obtained (body information and blood information) to be displayed on a screen and allows a doctor to recognize necessary information at a glance.

In the bed-side information system according to the present invention, the display means preferably predicts the body information and the blood information using neural network to display a predicted value.

This configuration also allows predicted information to be displayed on a screen and allows the doctor to recognize the trend of necessary information and take appropriate measures beforehand on the basis of this trend.

In the bed-side information system according to the present invention, the display means preferably comprises an analyzing section for converting retrieved blood information into blood information to be displayed as required, and calculating section for performing a calculation using neural network regarding the body information and the blood information to be displayed.

In the bed-side information system according to the present invention, the neural network preferably has input layer, intermediate layer, output layer, and weight between layers, the body information and the blood information to be displayed are input, a process using neural network is performed while controlling the weight on the basis of output of the intermediate layer and/or the output layer, and the body information and the blood information to be displayed are outputted.

In the bed-side information system according to the present invention, the display means preferably has warning means for setting an acceptable range of the body information and the blood information to be displayed to warn in the case of being out of the acceptable range.

This configuration makes it possible to immediately inform the doctor of the case of being out of the acceptable range and thereby allows the doctor to take appropriate measures immediately.

In the bed-side information system according to the present invention, the display means preferably displays acceptable ranges, current values, and trend-graphs of the body information and the blood information to be displayed on a screen.

This configuration allows all information obtained (body information and blood information) to be displayed on a screen, allows the doctor to recognize necessary information at a glance, recognize the trend of necessary information and take appropriate measures beforehand on the basis of the trend.

In the bed-side information system according to the present invention, the managing table preferably manages the body information, the blood information, predicted values of the body information and the blood information, acceptable ranges and current values of the body information and the blood information to be displayed, and information required to obtain information to be displayed.

The bed-side information system according to the present invention is characterized in that the body information is blood pressure, the blood information is Hematocrit, change blood volume rate, and Plasma Refilling Rate.

In the bed-side information system according to the present invention, the blood pressure is preferably calculated using autonomous nervous information and water balance information.

This configuration makes it possible to measure blood pressures as body information more accurately, thereby obtain accurate blood pressure information several hours later by predicting these parameters using neural network and allows the doctor to take appropriate measures.

DESCRIPTION OF THE PREFERRED EMBODIMENT(S)

Figure 1:
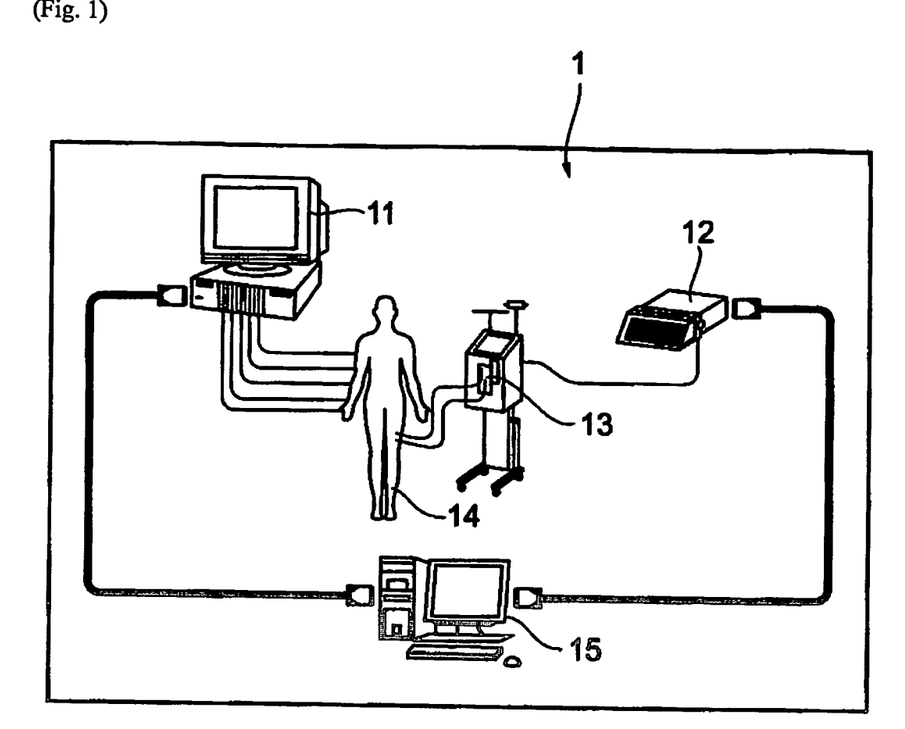
FIG. 1 is a view schematically showing an arrangement of a bed-side information system according to Embodiment of the present invention.

With reference now to the attached drawings, Embodiment of the present invention will be explained in detail below. FIG. 1 is a view schematically showing an arrangement of a bed-side information system according to Embodiment of the present invention.

The bed-side information system according to the present invention is principally constructed of a body information monitor (CMS) 11 which monitors arterial blood pressures, a Hematocrit monitor (CLM) 12 which monitors Hematocrit, change blood volume rate and venous blood oxygen saturation and a desktop PC 15 which displays these information items. The Hematocrit monitor 12 is connected to a blood circuit of a blood purifying device 13.

In this bed-side information system 1, the body information monitor 11 measures arterial blood pressures (ABP [mmHg]) of a patient 14. At this time, the body information monitor 11 measures systolic arterial blood pressures and diastolic arterial blood pressures and calculates mean arterial blood pressures thereof. Furthermore, the Hematocrit monitor 12 calculates Hematocrit (Ht [%]), change blood volume rate ($\Delta$BV % [%]) and venous blood oxygen saturation (vSpO$_2$ [%]).

The Hematocrit is a volume percentage of red blood cells in blood and $\Delta$BV % can be calculated using a value at the start of blood purification and a value after an arbitrary time has elapsed from the following Expression (1):

$$\Delta BV\%[\%] = [(Ht_{t=0}/Ht_{t=T}) - 1] \times 100 \quad \text{Expression (1)}$$

where $Ht_{t=0}$ is an Ht value at the start of blood purification and $Ht_{t=T}$ is an Ht value after a lapse of (arbitrary) time T.

Then, the body information monitor 11 sends information on arterial blood pressures to the desktop PC 15 and the Hematocrit monitor 12 sends information on the Hematocrit, change blood volume rate and venous blood oxygen saturation, etc., to the desktop PC 15. Then, the desktop PC 15 displays the arterial blood pressures (ABP), Hematocrit (Ht), change blood volume rate ($\Delta$BV (change rate of $\Delta$BV % for time t)) and plasma refilling rate (PRR [l/hr]) on a screen using these information items. At this time, PRR can be calculated using BV % from the following expression (2):

$$PRR[l/hr] = UFR + (BW \times TBV/100)/a \times [(\Delta BV/100)/\Delta t] \quad \text{Expression (2)}$$

where UFR[1/hr] is a water removing rate, a[kg/l] is specific gravity, BW[kg] is body weight of the patient, TBV[%] is the proportion of the total weight of blood in the body weight and $\Delta t$ is a $\Delta$BV % variation time.

Figure 2:
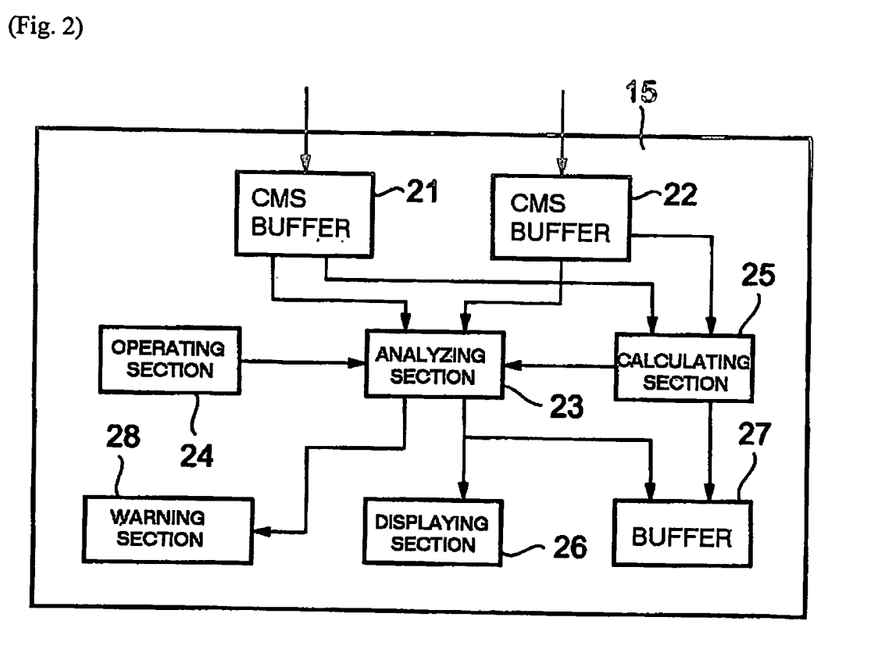
FIG. 2 is a block diagram showing an internal arrangement of desktop PC 15 in the bed-side information system according to Embodiment of the present invention.

FIG. 2 is a block diagram showing an internal arrangement of the desktop PC 15 in the bed-side information system according to the present invention. The desktop. PC 15 is principally constructed of a CMS buffer 21 which stores body information, a CLM buffer 22 which stores information on a change blood volume rate and venous blood oxygen saturation, an operating section 24 which inputs necessary information, an analyzing section 23 which analyzes the body information stored in the CMS buffer 21, the information stored in the CLM buffer 22 and information input from the operating section 24, a calculating section 25 which calculates a predicted value regarding the information analyzed by the analyzing section 23 using neural network, a displaying section which displays the information analyzed by the analyzing section 23 and/or predicted value calculated by the calculating section 25, a buffer 27 which stores information to be displayed and calculated information and a warning section 28 which warns in the case where a value is out of a predetermined acceptable range.

The arterial blood pressure information sent from the body information monitor 11 to the desktop PC 15 is stored in the CMS buffer 21. The information sent from the Hematocrit monitor 12 to the desktop PC 15 is stored in the CLM buffer 22. The information stored in the CMS buffer 21 and CLM buffer 22 is output to the analyzing section 23.

Figure 3:
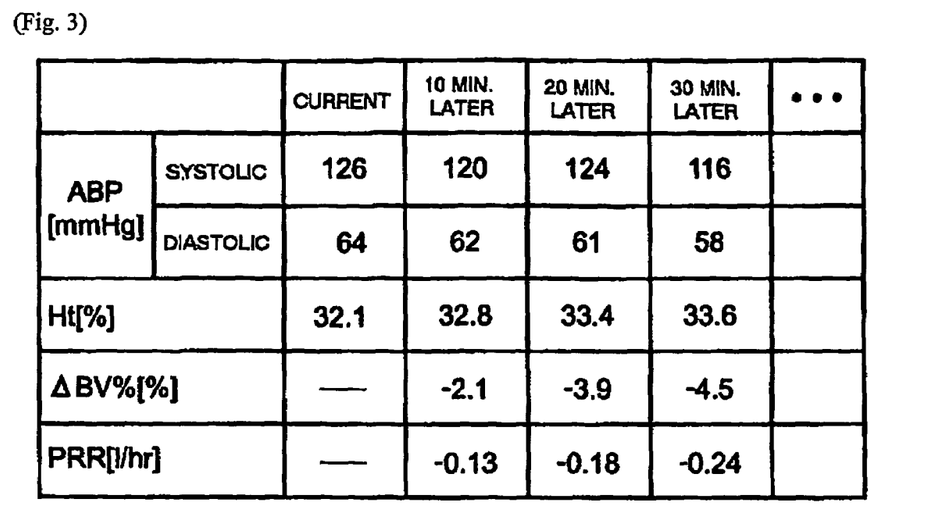
FIG. 3 is a view showing a managing table in the desktop PC of the bed-side information system according to Embodiment of the present invention.

The analyzing section 23 analyzes the information output from the CMS buffer 21 and CLM buffer 22 and controls information to be displayed on the displaying section 26. FIG. 3 is a view showing a managing table in the desktop PC of the bed-side information system according to the present invention. This managing table manages ABP values (systolic arterial blood pressures, diastolic arterial blood pressures, mean arterial blood pressures) from the body information monitor 11, Ht values and $\Delta$BV % values from the Hematocrit monitor 12, and PRR values calculated from $\Delta$BV %, body weight (BW) and water removing rate (UFR) input from the operating section 24 according to the above described Expression (2). The proportion of total weight of blood in the body weight (TBV) necessary to calculate PRR is preset (here 8%). Furthermore, the variation time of $\Delta$BV % ($\Delta$t) is calculated by the analyzing section 23.

The operating section 24 inputs the body weight (BW) and water removing rate (UFR) and also inputs warning values of various types of information, that is, upper limits and lower limits in a predetermined acceptable range based on the display screen which will be described later. Furthermore, the operating section 24 selects display items, maximum display time on the vertical axis of trend-graphs and display of prediction (prediction range, prediction time), etc. This managing table also manages information necessary to obtain information to be displayed, that is, information on the body weight (BW), water removing rate (UFR), warning values of various types of information, selection of display items, selection of maximum display time on the horizontal axis of trend-graphs or selection of display of prediction (prediction range, prediction time).

The information controlled by the analyzing section 23 is output to the displaying section 26. The displaying section 26 displays the information output from the analyzing section 23, that is, ABP value (systolic arterial blood pressures and diastolic arterial blood pressures), Ht value, ΔBV % value and PRR value on a screen at a time. An example of this display will be described later. Furthermore, the ABP value (systolic arterial blood pressures, diastolic arterial blood pressures, mean arterial blood pressures), Ht value and ΔBV % value, $vSpO_2$ value, BW, UFR and PRR value are sent from the analyzing section 23 to the buffer 27 and stored.

The calculating section 25 predicts an ABP value (systolic arterial blood pressures, diastolic arterial blood pressures, mean arterial blood pressures), Ht value and ΔBV % value and PRR value using neural network. Then, the prediction information is output to the analyzing section 23. The analyzing section 23 updates the predicted information items in the managing table shown in FIG. 3 one by one. Furthermore, the analyzing section 23 outputs the ABP value (systolic arterial blood pressures, diastolic arterial blood pressures), Ht value and ΔBV % value and PRR value including the predicted information to the displaying section 26. The displaying section 26 displays the ABP value (systolic arterial blood pressures, diastolic arterial blood pressures), Ht value and ΔBV % value and PRR value including the predicted information on a screen at a time. The managing table shown in FIG. 3 is an example and the present invention is not limited to this. Therefore, in the present invention, the information managed in the table is only required to include at least the information acquired from the body information monitor 11 and information acquired from the Hematocrit monitor 12 and the management items and layout of the table can be modified in various manners.

Figure 11:
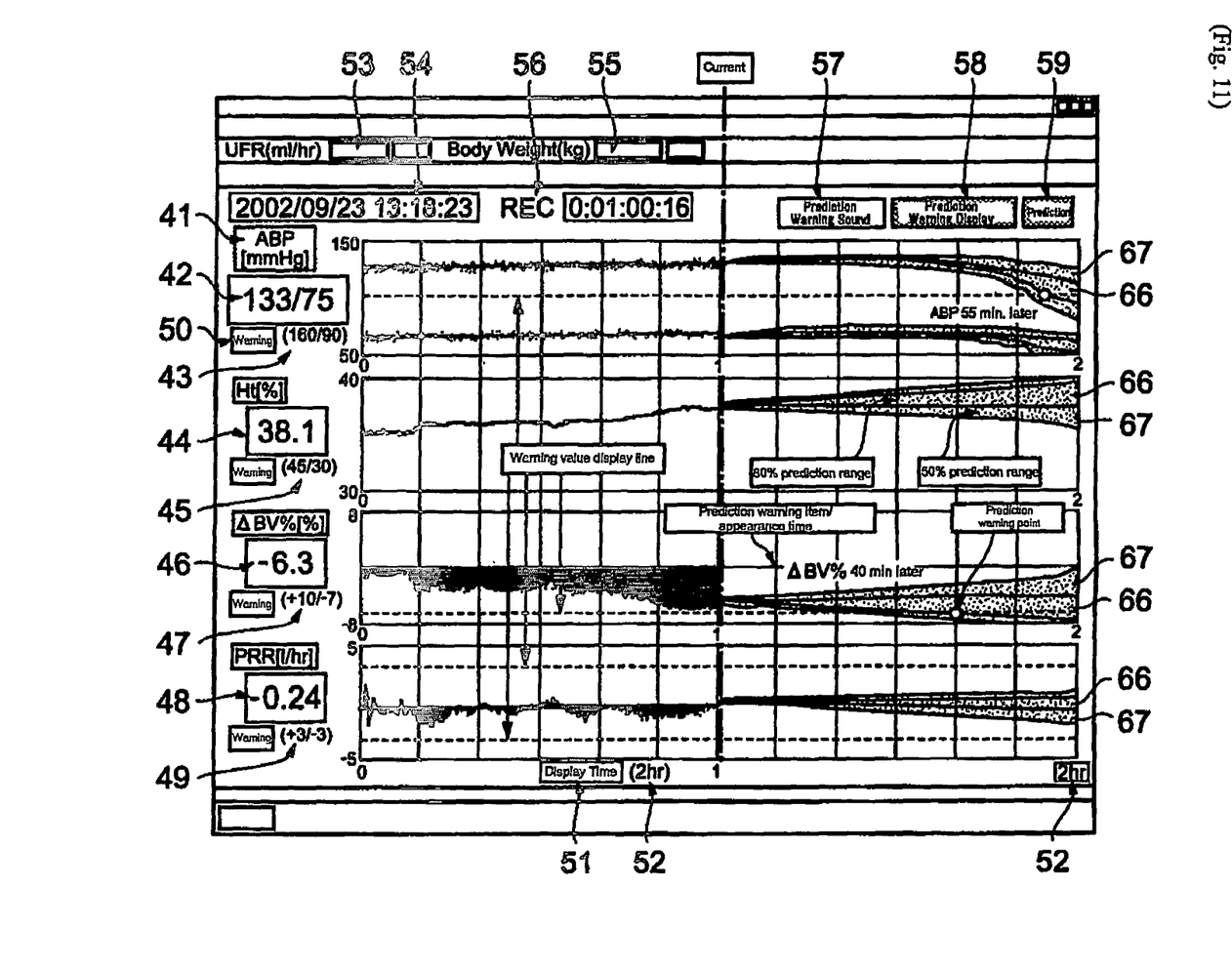
FIG. 11 is a view showing an example of the display on a screen in the bed-side information system according to Embodiment of the present invention.
Figure 12:
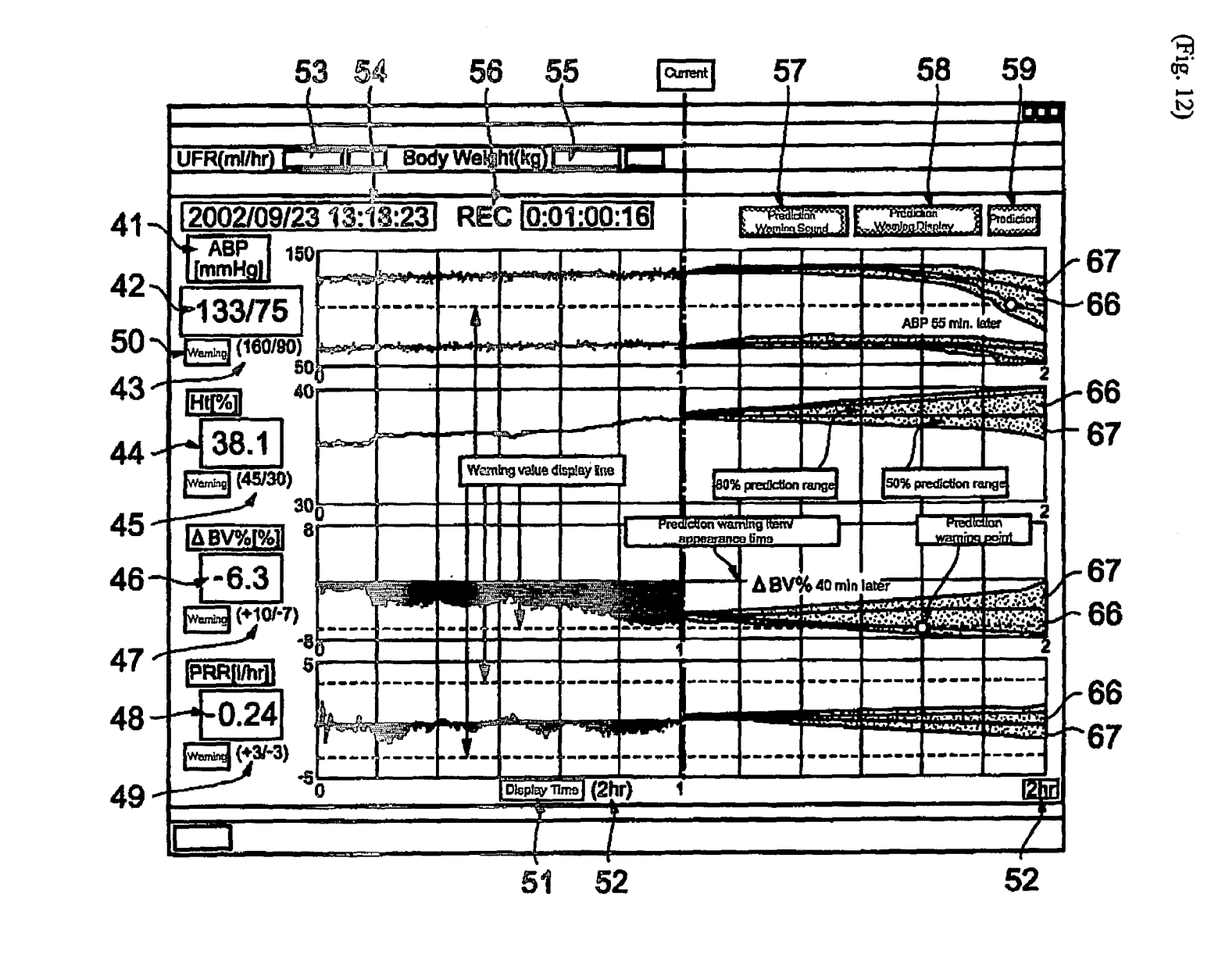
FIG. 12 is a view showing an example of the display on a screen in the bed-side information system according to Embodiment of the present invention.

With regard to the prediction information, the calculating section 25 calculates a predicted value within a selected prediction range, for example, a 50% prediction range or 80% prediction range. Furthermore, with regard to a prediction time, the calculating section 25 also calculates a predicted value regarding a selected prediction time. These prediction information items are also stored in the buffer 27. The preset prediction range and prediction time are not limited to these values but can be changed as appropriate. Furthermore, the predicted values calculated by the calculating section 25 are displayed as graphs on the displaying section 26 as shown in FIG. 11 and FIG. 12.

Furthermore, the calculating section 25 compares the warning set value input from the operating section 24 with the current value and if the current value is out of a predetermined acceptable range, the calculating section 25 outputs a control signal to the warning section 28. The warning section 28 warns based on the control signal. Warning may be performed by displaying a warning sign on a screen or outputting a warning sound.

Figure 4:
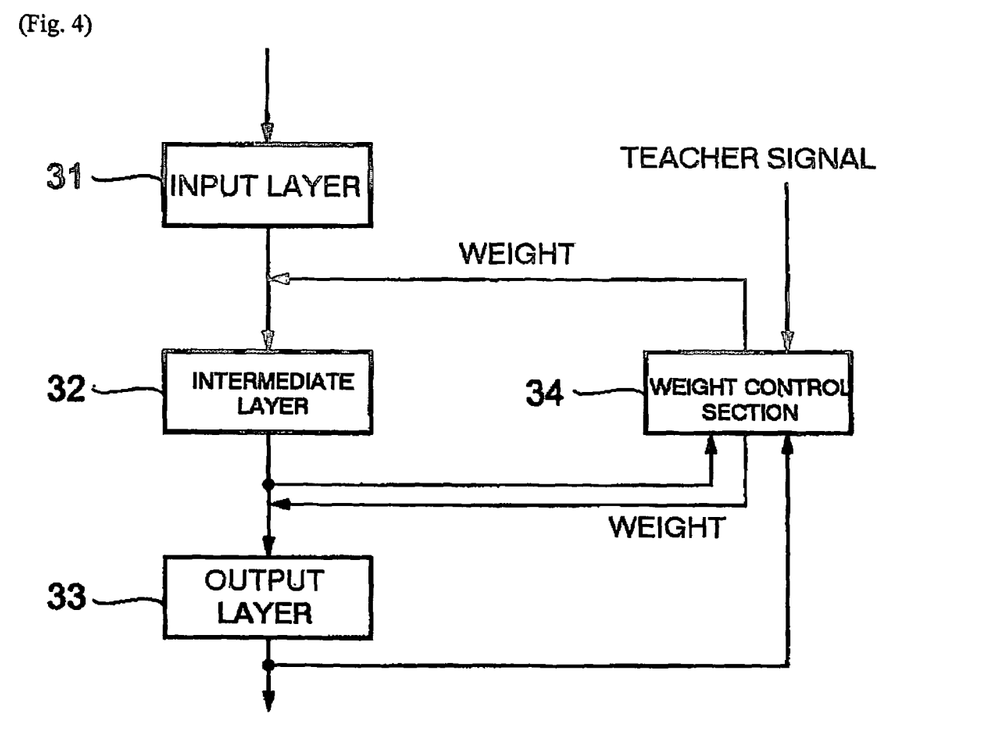
FIG. 4 is a block diagram for explaining a function of neural network.

FIG. 4 is a block diagram for explaining a function of neural network. The neural network is an information processing mechanism created by imitating the structure of a human brain and includes a layered type and interconnecting type. Here, a case where a back propagation learning type which is a typical example of the layered type is used will be explained. If it is possible to predict ABP values (systolic arterial blood pressures, diastolic arterial blood pressures), Ht value, ΔBV % value and PRR value, any neural network other than the back propagation learning type can also be used.

The neural network is principally constructed of an input layer 31, an intermediate layer 32, an output layer 33 and weight between layers. This weight is controlled by a weight control section 34 based on the output of the intermediate layer 32 and/or output layer 33. Here, suppose the input layer 31 has 6 units, the intermediate layer 32 has 30 units and the output layer 33 has 1 unit. Furthermore, the input layer 31 and intermediate layer 32 each include a unit for inputting a fixed value (bias) as an offset. Thus, the neural network has a plurality of input units and one output unit, calculates a weighted sum of all input values using the weights assigned to the respective units and then applies certain nonlinear conversion and sends the converted values to the output layer. At this time, the weight control section 34 is given a teacher signal as a correct answer. The weight control section 34 calculates an error between the output and teacher signal (mean square error) and controls the weights from the error based on a back propagation leaning rule. This controlled weight is assigned to each unit. Processing (learning) is repeatedly performed so as to reduce this mean square error. The processing of the neural network is carried out in this way.

In the bed-side information system of the present invention, when, for example, continuous hemofiltration therapy is in progress, six signals are input to the input layer 31 every 20 seconds and a seventh signal after 20 seconds is predicted and output. More specifically, when a learning coefficient is assumed to be 0.003, if the learning count exceeds approximately 100, the mean square error becomes 0.48 and even if the learning count increases further, the mean square error becomes constant. In this way, six signals are input to the input layer 31 every 20 seconds and the seventh signal after 20 seconds is predicted and output. The predicted value obtained in this way is output to the analyzing section 23 and displayed on the displaying section 26.

Thus, it is possible to predict each information item after approximately 20 seconds and also display the predicted information on a screen. Here, for simplicity of explanation, a case where six signals are input and the seventh signal is predicted and output has been explained, but it is possible to predict up to information after several hours by changing the structure of the neural network (by changing the number of units, learning coefficient, number of intermediate layers). This allows the doctor to take appropriate measures based on the predicted information.

Next, an example of the display on a screen in the bed-side information system according to Embodiment of the present invention will be explained. FIG. 5 to FIG. 12 show examples of the display on a screen in the bed-side information system according to Embodiment of the present invention.

This embodiment will explain a case where the body information is arterial blood pressures (ABP) and blood information is Hematocrit (Ht), change blood volume rate (ΔBV %) and plasma refilling rate (PRR), but the body information and blood information of the present invention are not limited to these information items and can be changed in various ways.

Figure 5:
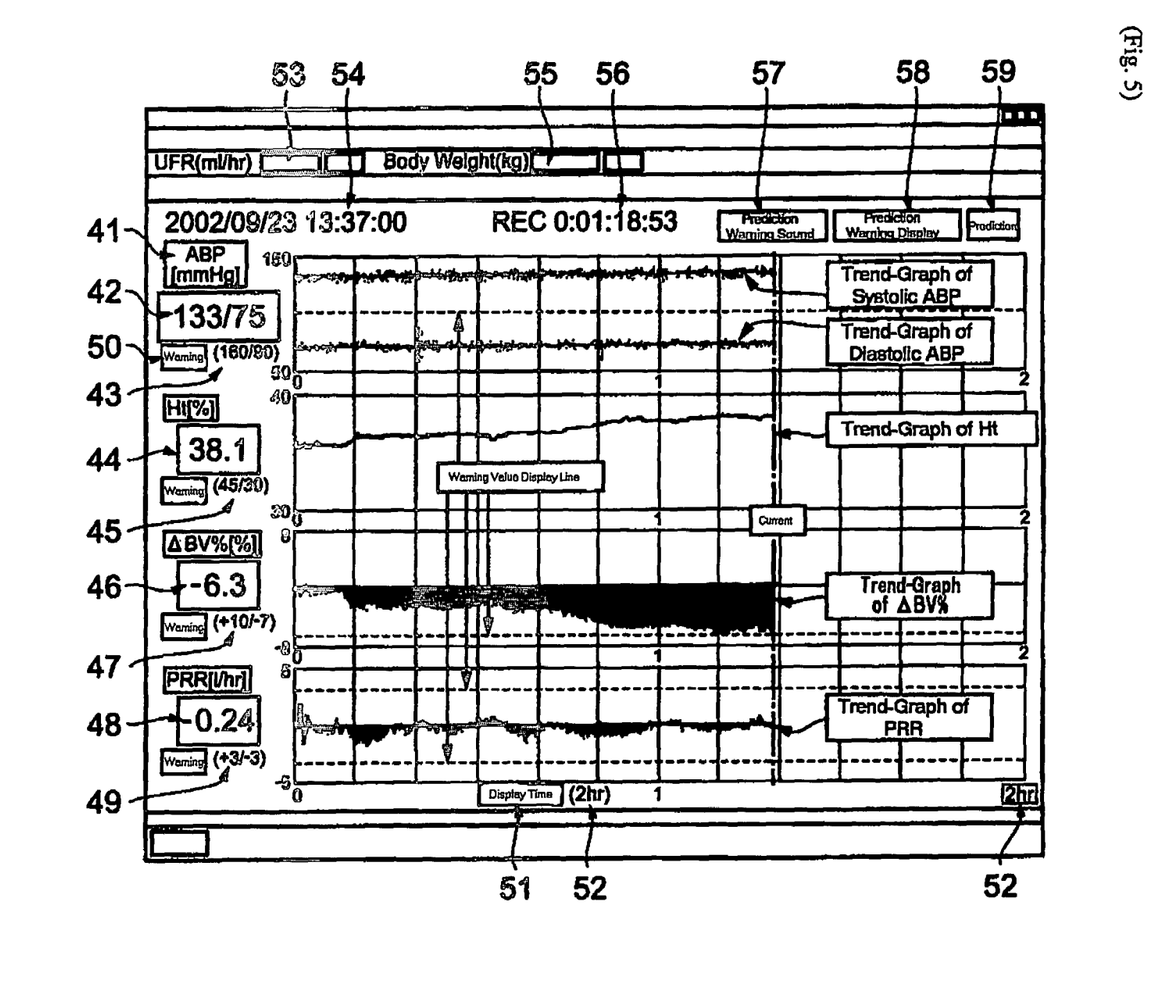
FIG. 5 is a view showing an example of the display on a screen in the bed-side information system according to Embodiment of the present invention.

On the left of the screen in FIG. 5 are an ABP display item selection button 41, ABP current value display area 42, systolic ABP warning set value (upper/lower limit) display area 43, Ht current value display area 44, Ht warning set value (upper/lower limit) display area 45, ΔBV % current value display area 46, ΔBV % warning set value (upper/lower limit) display area 47, PRR current value display area 48 and PRR warning set value (upper/lower limit) display area 49. Furthermore, on the left of the screen are warning buttons 50 to warn (e.g., issue an alarm sign) in case of being out of a predetermined acceptable range provided for the respective information items and pressing these buttons makes it possible to input an upper/lower limit (warning set value (upper/lower limit) within a predetermined acceptable range.

At the bottom of the screen are a display time selection button 51 and a maximum display time display area 52. At the top of the screen are a water removing rate display area 53, a current time display area 54, a body weight display area 55, an elapsed time display area 56, a prediction warning sound button 57, a prediction warning display button 58 and a prediction button 59.

The screen further displays a trend-graph of systolic ABP, trend-graph of diastolic ABP, trend-graph of Ht, trend-graph of ΔBV % and trend-graph of PRR and shows a warning value display line specific to each information item. This warning value display line can be changed based on the setting of the warning value which will be described later as appropriate.

Figure 6:
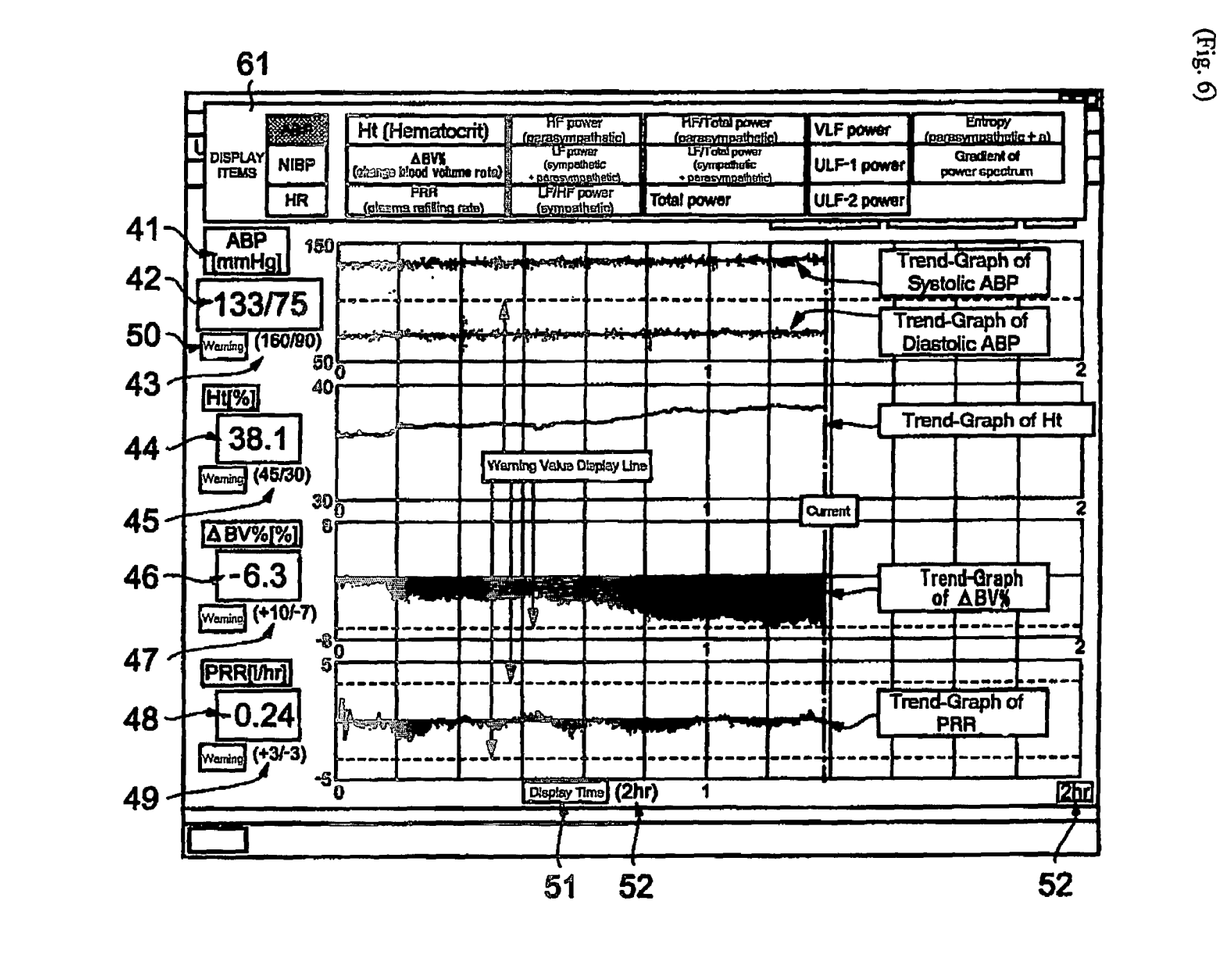
FIG. 6 is a view showing an example of the display on a screen in the bed-side information system according to Embodiment of the present invention.

On this display screen, pressing the display item selection button 41 shows a display item area 61 as shown in FIG. 6. Here, it is possible to select items to be displayed on the screen (body information and blood information to be displayed). Here, when information is selected, the analyzing section 23 refers to the managing table, extracts the selected information and displays it on the screen.

Figure 7:
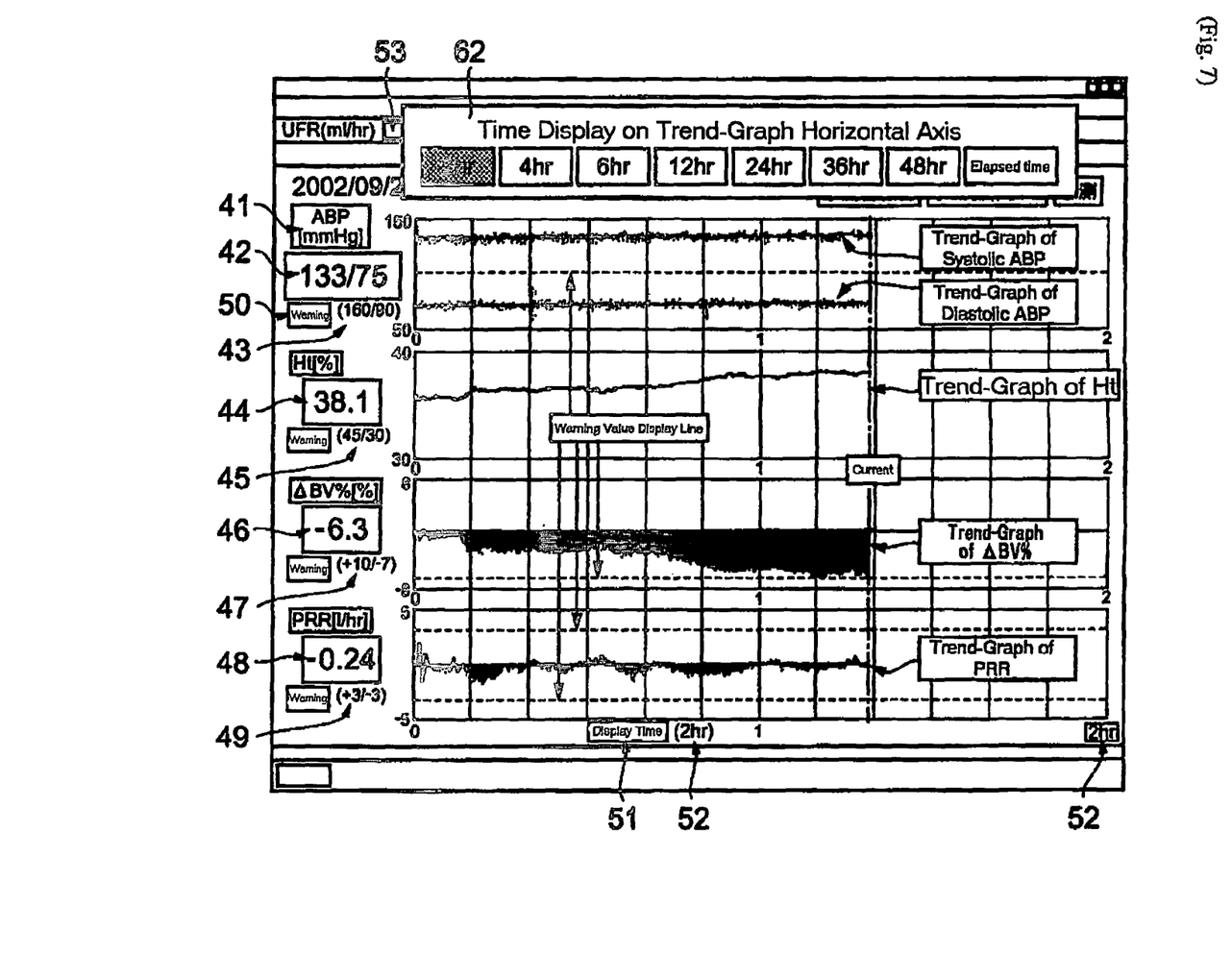
FIG. 7 is a view showing an example of the display on a screen in the bed-side information system according to Embodiment of the present invention.

Pressing the trend-graph display time selection button 51 shows a display time area 62 on the trend-graph horizontal axis as shown in FIG. 7. Here, if a maximum display time on the horizontal axis of the trend-graph is selected, the scale on the horizontal axis of the trend-graph is changed according to the maximum display time selected. Furthermore, the selected maximum display time is displayed in the maximum display time display area 52.

Figure 8:
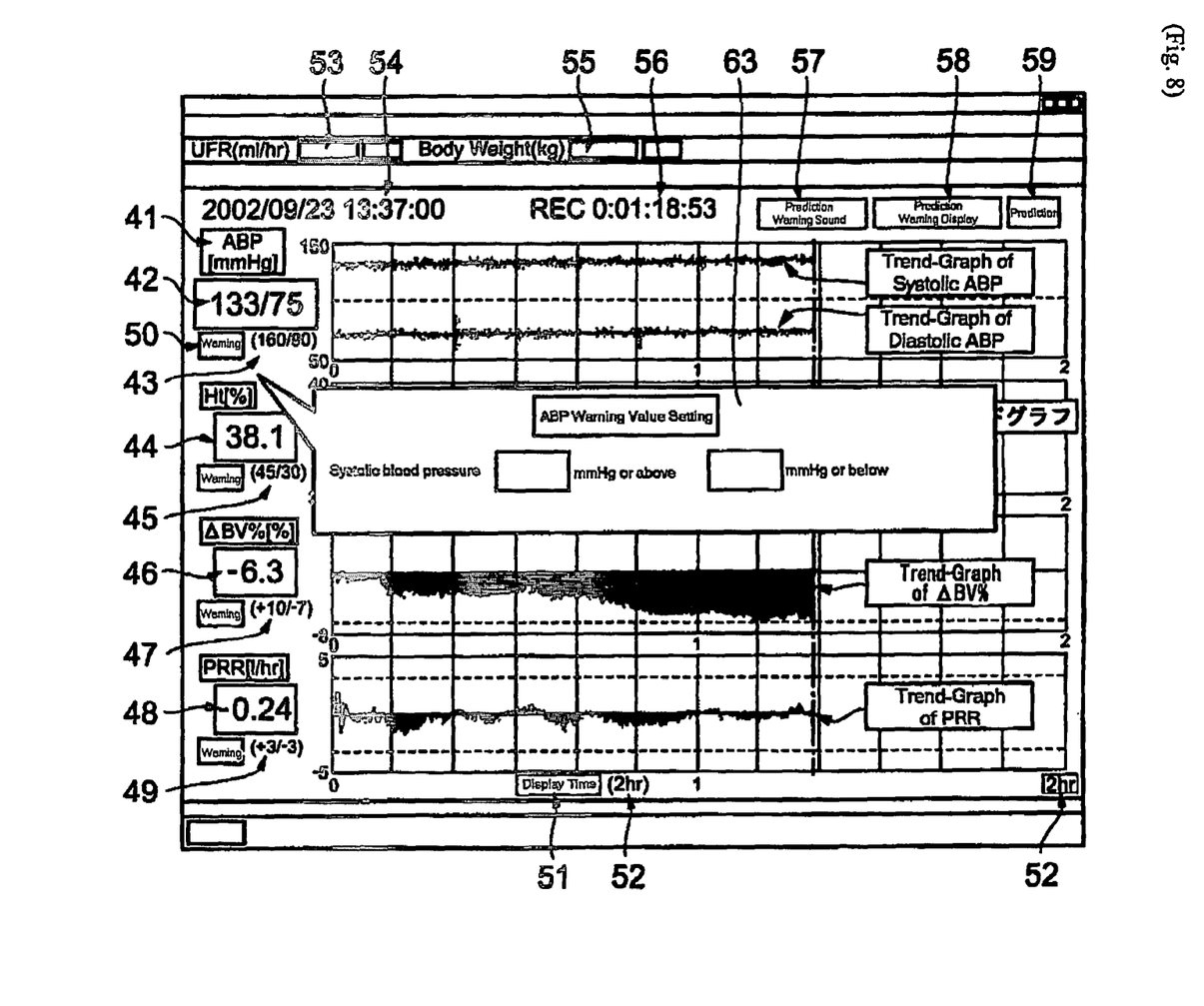
FIG. 8 is a view showing an example of the display on a screen in the bed-side information system according to Embodiment of the present invention.

Pressing a warning button, for example, the ABP warning button shows an ABP warning value setting area 63 as shown in FIG. 8. Here, entering a lower limit and upper limit of systolic blood pressures shows an upper limit value and a lower limit value in the systolic ABP warning set value (upper/lower limit) display area 43. The same applies to other information (Ht, ΔBV %, PRR) and pressing the warning button and entering the lower limit value and upper limit value causes the Ht warning set value (upper/lower limit) display area 45, ΔBV % warning set value (upper/lower limit) display area 47 and PRR warning set value (upper/lower limit) display area 49 to display their respective upper limit and lower limit values.

Figure 9:
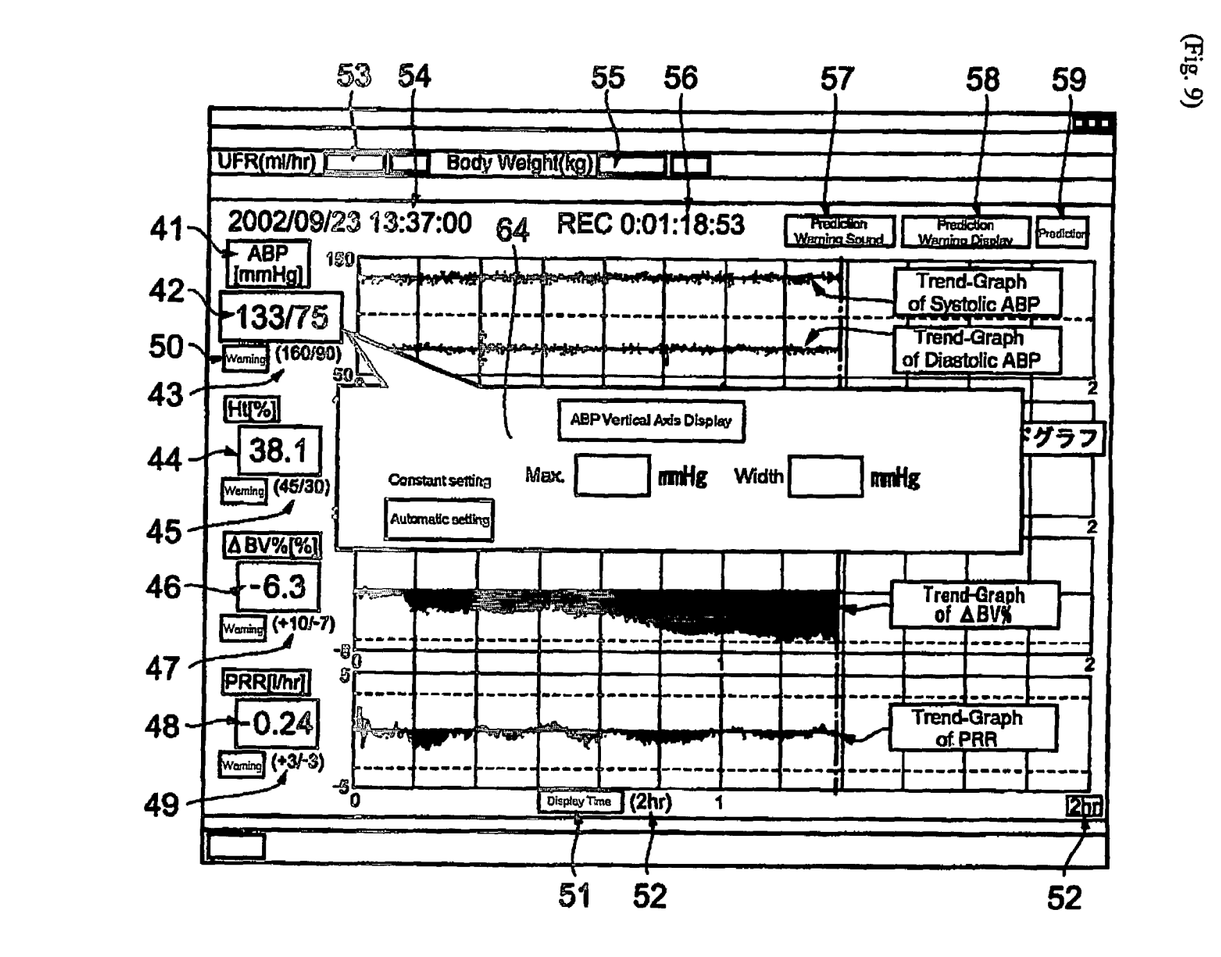
FIG. 9 is a view showing an example of the display on a screen in the bed-side information system according to Embodiment of the present invention.

Pressing a current value display area, for example, the ABP current value display area 42 shows an ABP vertical axis display area 64 as shown in FIG. 9. Here, entering a maximum value and width sets the display scale of an ABP trend-graph and displays the ABP trend-graph on that scale. The same applies to other information items (Ht, ΔBV %, PRR) and pressing the current value display areas 44, 46 and 48 and entering a maximum value and width causes the Ht current value display area 44, ΔBV % current value display area 46 and PRR current value display area 48 to display their respective maximum values and widths. Selecting an automatic setting on the display of the ABP vertical axis automatically shows a preset maximum value and width or a maximum value and width of measured values for a certain period of time that can be displayed in the current value display area.

Figure 10:
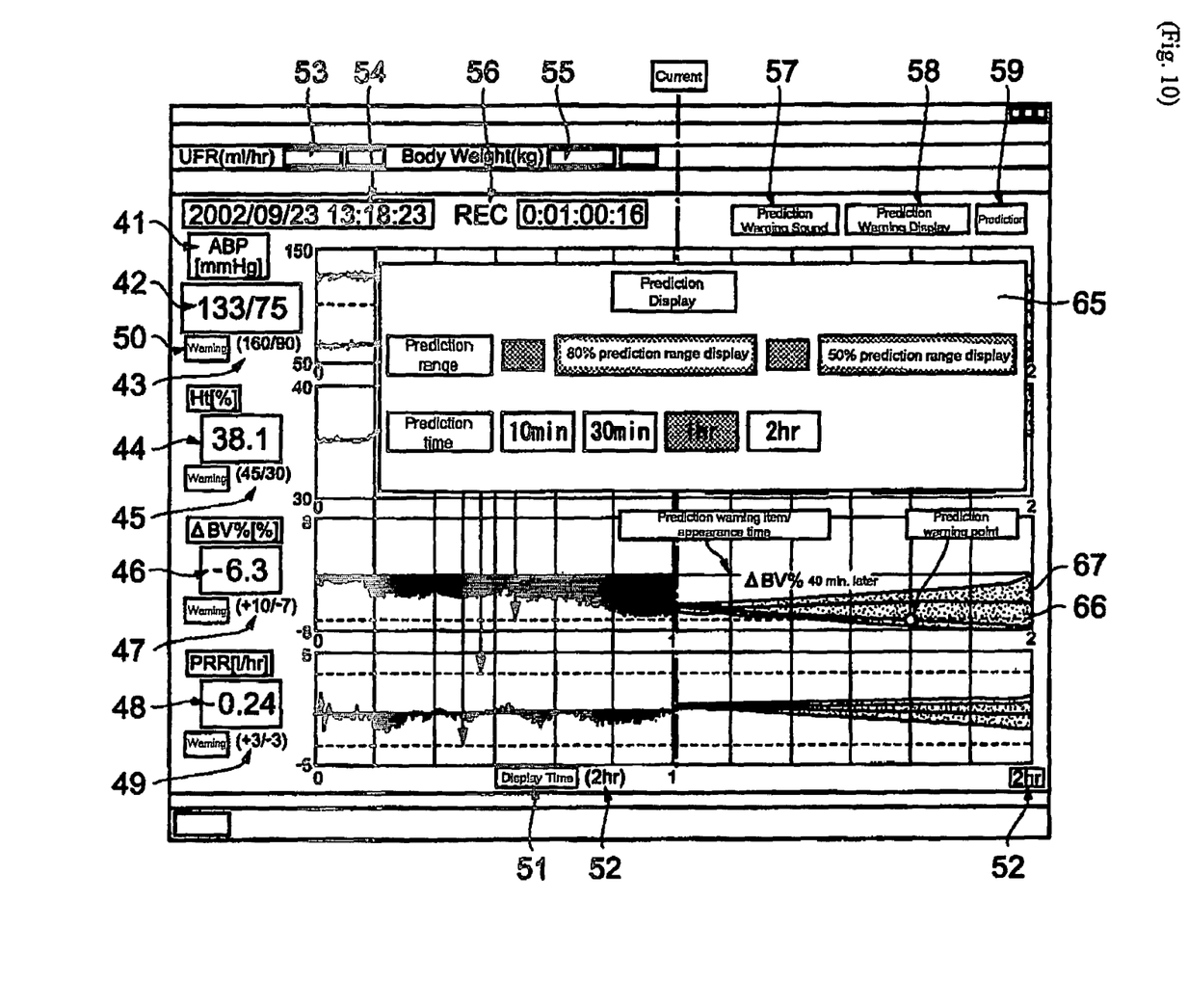
FIG. 10 is a view showing an example of the display on a screen in the bed-side information system according to Embodiment of the present invention.

Pressing the prediction button 59 shows a prediction display area 65 as shown in FIG. 10. Here, selecting a prediction range and prediction time shows prediction information corresponding to only the prediction range and prediction time. For example, a 50% prediction range 67 is displayed outside and an 80% prediction range 66 is displayed inside in FIG. 11 and FIG. 12. It is preferable to show the 50% prediction range 67 and 80% prediction range 66 color-coded to be easily readable. Here, up to prediction information several hours later is displayed on the screen using neural network having a structure which makes it possible to obtain prediction information several hours later.

As shown in FIG. 11, pressing the prediction warning display button 58 shows a prediction warning point for each information item. When this prediction warning point is reached, a warning is displayed. Furthermore, as shown in FIG. 12, pressing the prediction warning sound button 57 outputs a warning sound when the prediction warning point is reached.

Such a display shows all information items obtained (body information and blood information) on a screen and allows the doctor to recognize necessary information at a glance. Furthermore, since prediction information can also be displayed on a screen, it is possible to recognize the trend of necessary information and the doctor can take appropriate measures beforehand based on the trend.

This embodiment has explained the case where information on arterial blood pressures is used as body information, but it is also possible to use noninvasive blood pressures (NIBP) or cardiac rate as the body information. Furthermore, it is also possible to acquire and display peripheral vascular resistance and cardiac output as the body information as factors determining a blood pressure.

A blood pressure is considered to be affected by elasticity of blood vessels, pulsation, cardiac contractile force, circulating blood volume, thickness of blood vessels and blood viscosity. Among these factors, elasticity of blood vessels, thickness of blood vessels and blood viscosity are related to the above-described peripheral vascular resistance, while pulsation, cardiac contractile force and circulating blood volume are related to the above described cardiac output Among these factors, elasticity of blood vessels, pulsation, cardiac contractile force and thickness of blood vessels are affected by autonomic nerve, while circulating blood volume and blood viscosity are affected by water balance.

Therefore, directly measuring or calculating these parameters makes it possible to obtain accurate blood information. Thus, predicting these parameters using neural network makes it possible to obtain accurate blood pressure information even up to several hours later and allows the doctor to take more appropriate measures.

Furthermore, it is also possible to collect waveform information of an electrocardiogram as autonomic nerve information in a computer, analyze pulsation variation (variation in intervals between R-waves in a electrocardiogram; R-wave refers to the highest part in an electrocardiogram waveform of one pulse) using, for example, a maximum entropy method, calculate and display the following indices as shown in FIG. 6.

(1) Index indicating activity (LF/HF power (ratio of LF power to HF power))

(2) Indices indicating activity of parasympathetic nerve (HF power (power (msec×msec) of high frequency component of 0.15 to 0.4 Hz), HF/Total power (ratio of HF power to total power), entropy (disorder of beat intervals, amount of data to be analyzed is less than 4 sec, including autonomic nerve activity other than activity of parasympathetic nerve))

(3) Indices indicating activity of sympathetic nerve+parasympathetic nerve (LF power (power (msec×msec) of low frequency component of 0.04 to 0.15 Hz, amount of data to be analyzed requires 30 sec, values are displayed every 2 sec), LF/total power (ratio of LF power to total power))

(4) Other indices concerning autonomic nerve (total power (power of all frequency components), VLF power (power (msec×msec) of frequency component of 0.003 to 0.04 Hz, amount of data to be analyzed requires 300 sec, values are displayed every 4 sec), ULF-1 power (power (msec×msec) of frequency component of $1/10,000$ to $1/2,000$ Hz, amount of data to be analyzed requires 1000 sec, values are displayed every 16 sec), ULF-2 power (power (msec×msec) of frequency component of $1/2,000$ to 0.003 Hz, amount of data to be analyzed requires 1800 sec, values are displayed every 8 sec), gradient of power spectrum (gradient of power spectrum in a frequency band of $1/10,000$ to $1/100$ Hz, amount of data to be analyzed is 10000 sec, values are displayed every approximately 30 sec, one of indices expressing comfort)

In this embodiment, information which seems to be the cause for affecting the body, for example, information on chemicals administered to the body or information known from the amount of water content and excretions of a patient can also be additionally used for prediction using neural network. This makes it possible to accurately obtain a predicted value and allows the doctor to take appropriate measures.

The present invention is not limited to the above-described embodiment and can also be implemented modified in various ways. For example, the numerical values and display items in the above-described embodiment are only examples and the present invention is not limited to them and can be implemented modified in various ways.

As described above, the present invention comprises body information acquiring means for acquiring body information of a patient, blood purifying means for purifying blood of the patient, the blood purifying means having a blood circuit for circulating the blood, blood information acquiring means for acquiring blood information obtained from the blood, the blood information acquiring means connecting to the blood circuit, and display means for displaying the body information and the blood information, the display means connecting to the body information acquiring means and the blood information acquiring means, wherein the display means displays the body information and the blood information on a screen, and can thereby display necessary information on the same screen and display predicted information obtained by predicting the progression of necessary information on the same screen.

This application is based on the Japanese Patent Application No 2003-040931 filed on Feb. 19, 2003, entire content of which is expressly incorporated by reference herein.

The invention claimed is:

1. A bed-side information system comprising:
 body information acquiring means for acquiring body information of a patient;
 blood purifying means for purifying blood of said patient, said blood purifying means having a blood circuit for circulating the blood;
 blood information acquiring means for acquiring blood information obtained from the blood, said blood information acquiring means connecting to said blood circuit; and
 display means for displaying said body information and said blood information, said display means connecting to said body information acquiring means and said blood information acquiring means,
 wherein said display means predicts said body information and said blood information using a neural network to display a predicted value.

2. The bed-side information system according to claim 1, wherein said display means has warning means for setting an acceptable range of said body information and said blood information to be displayed to warn in the case of being out of said acceptable range.

3. The bed-side information system according to claim 1, wherein said display means displays acceptable ranges, current values, and trend-graphs of said body information and said blood information to be displayed on a screen.

4. The bed-side information system according to claim 1, wherein said display means has a managing table for managing said body information and said blood information, and displays said body information and said blood information on a screen according to said managing table, and wherein said managing table manages said body information, said blood information, predicted values of said body information and said blood information, acceptable ranges and current values of said body information and said blood information to be displayed, and information required to obtain information to be displayed.

5. The bed-side information system according to claim 1, wherein said body information is blood pressure, said blood information is Hematocrit, change blood volume rate, and Plasma Refilling Rate.

6. The bed-side information system according to claim 1, wherein said blood pressure is calculated using autonomous nervous information and water balance information.

7. The bed-side information system according to claim 1, wherein said display means calculates at least one predicted value within a selected prediction range and wherein said display means calculates said at least one predicted value over a selected prediction time.

8. The bed-side information system according to claim 7, wherein said display means displays said at least one predicted value as a graph within the selected prediction range over said selected prediction time.

9. The bed-side information system according to claim 1, wherein said display means comprises an analyzing section for converting retrieved blood information into blood information to be displayed, and a calculating section for performing a calculation using said neural network regarding said body information and said blood information to be displayed.

10. The bed-side information system according to claim 9, wherein said neural network has input layer, intermediate layer, output layer, and weight between layers, said body information and said blood information to be displayed are input, a process using said neural network is performed while controlling said weight on the basis of output of said intermediate layer and/or said output layer, and said body information and said blood information to be displayed are outputted.

11. The bed-side information system according to claim 9, wherein said calculating section calculates at least one predicted value within a selected prediction range and wherein said calculating section calculates said at least one predicted value over a selected prediction time.

12. The bed-side information system according to claim 11, wherein said display means displays said at least one predicted value as a graph within the selected prediction range over said selected prediction time.

13. A bed-side information system comprising:
a body information acquiring unit configured to acquire body information of a patient;
a blood purifying unit configured to purify blood of said patient, said blood purifying unit having a blood circuit for circulating the blood;
a blood information acquiring unit configured to acquire blood information obtained from the blood, said blood information acquiring unit connecting to said blood circuit; and
a display unit configured to display said body information and said blood information, said display unit being connected to said body information acquiring unit and said blood information acquiring unit, said display means including:
an analyzing section configured to convert retrieved blood information into blood information to be displayed, and
a calculating section configured to perform a calculation using a neural network regarding said body information and said blood information to be displayed.

14. A bed-side information system according to claim 13, wherein said display unit includes a warning unit configured to set an acceptable range of said body information and said blood information to be displayed to warn in the case of being out of said acceptable range.

15. The bed-side information system according to claim 13, wherein said display unit displays acceptable ranges, current values, and trend-graphs of said body information and said blood information to be displayed on a screen.

16. The bed-side information system according to claim 13, wherein said display unit includes a managing table configured for managing said body information and said blood information, and displays said body information and said blood information on a screen according to said managing table, and wherein said managing table manages said body information, said blood information, predicted values of said body information and said blood information, acceptable ranges and current values of said body information and said blood information to be displayed, and information required to obtain information to be displayed.

17. The bed-side information system according to claim 13, wherein said body information includes blood pressure, said blood information includes Hematocrit change blood volume rate, and Plasma Refilling Rate.

18. The bed-side information system according to claim 13, wherein said blood pressure is calculated using autonomous nervous information and water balance information.

* * * * *